United States Patent [19]

Patroni et al.

[11] Patent Number: 4,992,531

[45] Date of Patent: * Feb. 12, 1991

[54] PRODUCTION OF PROTEINS IN ACTIVE FORMS

[75] Inventors: Joseph J. Patroni, West Preston; Malcolm R. Brandon, Ivanhoe, both of Australia

[73] Assignee: Bunge (Australia) Pty. Ltd., Melbourne, Australia

[*] Notice: The portion of the term of this patent subsequent to Jan. 10, 2006 has been disclaimed.

[21] Appl. No.: 206,006

[22] Filed: Jun. 13, 1988

[30] Foreign Application Priority Data

Jun. 15, 1987 [AU] Australia .................................. PI2472

[51] Int. Cl.$^5$ .......................... C07K 3/12; C07K 3/28; C07K 15/08; C07K 15/26
[52] U.S. Cl. .................................. 530/351; 530/350; 530/399; 530/412; 530/413; 530/414; 530/416; 530/417; 530/422; 435/69.1; 435/69.4; 435/69.51; 435/69.5
[58] Field of Search ............... 435/68, 69.4, 69.5; 530/412, 413, 414, 416, 417, 422, 351, 350, 399

[56] References Cited

U.S. PATENT DOCUMENTS

| 4,476,049 | 10/1984 | Kung .................................. 260/112 |
| 4,677,196 | 6/1987 | Rausch et al. ..................... 530/412 |
| 4,681,761 | 7/1987 | Mietzner ............................ 424/92 |
| 4,797,474 | 1/1989 | Patroni et al. .................... 530/351 |

OTHER PUBLICATIONS

Sharma, S. K., 1986, Separation Science and Technology, 21(8):701–726.
Moriyama et al., 1985, Biochimica et Biophysica Acta., 832:135–141.

Primary Examiner—Margaret Moskowitz
Assistant Examiner—Keith C. Furman
Attorney, Agent, or Firm—Merchant, Gould, Smith, Edell, Welter & Schmidt

[57] ABSTRACT

A method for the recovery of proteins in a solubilized form from host cells including providing a source of host cells incorporating a synthesized or expressed protein; providing a source of at least one cationic surfactant; and treating the host cells with at least one cationic surfactant, in an amount sufficient to effect solubilization of the proteins.

6 Claims, No Drawings

PRODUCTION OF PROTEINS IN ACTIVE FORMS

BACKGROUND OF THE INVENTION

The present invention relates to a method for the preparation of a protein in a biologically active or native form.

Recombinant DNA technology provides potentially extremely valuable means of synthesizing amounts of desirable eukaryotic (usually mammalian) proteins such as hormones, interferons, and enzymes. Although it has proved to be relatively easy to manipulate organisms such as bacteria to produce the desired protein, the host organism may not secrete the over-produced protein product into the culture medium. Thus physical or chemical lysis of the organisms (for example bacteria), followed by mechanical isolation of the insoluble desired protein is usually necessary. In the prior art, solubilization of the insoluble protein then proceeds with high concentrations of denaturants such as an aqueous urea or guanidine hydrochloride (International patent application WP 83/04418). Thus, solubilization has been conducted with relatively pure forms of the desired protein being obtained by a multistep process. Such processes are capital intensive and are best avoided when applied industrially.

In copending Australian patent application 66874/86, applicants have described a highly advantageous, albeit multistep, economical method for the recovery of proteins in a soluble form from an insoluble protein source utilising a cationic surfactant. While this process allows for the efficient recovery of proteins in a soluble form, the ultimate recovery of active protein has been limited. For example, the overall recovery is normally less than 50%. Significant losses may occur in the collection of host cells, their lysis and concentration of protein aggregates thus released via physical concentrative methods including differential centrifugation.

SUMMARY OF THE INVENTION

Accordingly, it is an object of the present invention to overcome, or at least alleviate, one or more of the difficulties related to the prior art.

Accordingly, in a first aspect, there is provided a method for the recovery of proteins comprising the steps of:
providing a source of host cells incorporating a synthesized or expressed protein; and
providing a source of at least one cationic, anionic or zwitterionic surfactant (tenside); and
treating the host cells with the at least one cationic, anionic or zwitterionic surfactant (tenside) in an amount sufficient to effect protein solubilization.

Preferably, the method for recovery of proteins further comprises providing a fermentation broth including host cells incorporating a synthesized or expressed protein and isolating the host cells therefrom. The isolation step may be undertaken utilizing any suitable method. Flotation, centrifugation, filtration or ultrafiltration may be used.

For many host cells, the cationic, anionic or zwitterionic surfactant may also function to lyse the cells. However, where this does not occur, a further mechanical or chemical lysis step may be preferred. In this situation, the treatment is undertaken on the concentrated, relatively impure whole cell lysate.

The host cell, in a preferred aspect, may be pretreated to kill the cell or weaken the cell membrane to facilitate lysis.

In a preferred aspect the method of recovery according to the present invention further comprises the simultaneous step of:
lysing the host cells to form a whole cell lysate.

The product solution so formed may be purified utilizing either differential centrifugation, differential precipitation, chromatography or filtration. This will remove impurities such as insoluble unwanted contaminants, unwanted cell debris and other unwanted macromolecules.

Desirably, the amount of the at least one cationic, anionic or zwitterionic surfactant exceeds the critical micelle concentration.

DETAILED DESCRIPTION OF THE PREFERRED EMBODIMENT

The present invention is particularly applicable to the solubilization and recovery of biologically important proteins synthesized by microorganisms and eukaryotic cell lines which have been modified by recombinant DNA technology. The desired protein may comprise an inclusion body in a host cell which may have been transformed or transfected with a vector, including a gene coding for the protein.

The protein which may be recovered according to the present invention may be selected from monomeric and polymeric intracellular proteins such as those found in cellular inclusion bodies and cytoplasmic aggregates. The inclusion bodies may be selected from biologically important polypeptides and peptides including porcine, orine and bovine growth hormones, interferons, immunogens and lymphokines, or heterogeneous or homogeneous polymers thereof.

Preferably, at least one cationic, anionic or zwitterionic surfactant is present in an amount from approximately 2.5 to 50% weight/volume, more specifically 2.5 to 20% weight/volume. The upper limit of surfactant content may vary and be limited by the solubility of the selected surfactant.

We have found that it is possible to solubilise aggregates of desired proteins produced and contained within whole cells, including inclusion bodies, by treatment of the cell and its components with a surfactant in water, either in the presence or absence of a polar organic solvent or with the polar aqueous solvent alone. The process can be rapid (5-60 min), and optimal of the solubilized protein can be easily effected. Only small quantities of inexpensive reagents, which are readily available and recyclable, are required. For example, the bulk of the solubiling agent may be water.

According to a preferred aspect of the present invention there is provided a method for the recovery of cellular proteins, which method includes providing a source of host cells incorporating the desired protein providing a source of at least one cationic, anionic or zwitterionic surfactant and a source of at least one polar organic solvent; treating the cells with a mixture of approximately 5 to 70% volumes/volume of at least one polar organic solvent and at least one cationic, anionic or zwitterionic surfactant in an amount sufficient to effect cell lysis and protein solubilization without substantial modification to the structural backbone of the protein; and separating the protein from the resulting mixture.

The protein may be maintained in an aqueous solution comprising a polar organic solvent and suitable buffering salts. Preferably, the pH of the solution is optimized to ensure protein solubility and stability of the solution. The presence of a polar organic solvent, such as acetonitrile or acetic acid, preferably at a concentration of 5 to 70% alters the interaction between the insoluble protein and the aqueous solvent, thereby facilitating the solubility of the hydrophobic regions of the protein. More, preferably the concentration of the organic solvent is 10 to 20%.

Moreover, the incorporation of a cationic surfactant, such as a quaternary ammonium compound, at a level exceeding the critical micelle concentration and sufficient to overcome the associative forces of the cell wall and those within the protein aggregate, is highly advantageous and promotes lysis of the cell, and the segregation, disruption and solubilization of the inclusion body constituents.

The method may be conducted at any suitable temperature above the freezing point of the solution. A temperature in the range of approximately 4° to 25° C. is preferred.

According to another embodiment of the invention, the addition of an aqueous solution of a suitable surfactant to a dried powder or an aqueous slurry of the host cells is also a desirable and efficient means of solubilization of cellular proteins. The addition of the at least one cationic, anionic or zwitterionic surfactant is at levels above the critical micelle concentration and within the limit of its solubility and economy.

In contrast to some prior art, the proteins may be solubilized in a mild, near neutral environment. Furthermore, only low concentrations of the solubilizing agents are required, and these may be readily removed. Due to the chemical nature of the solubilizing agent, the recovery method is compatible with later processing steps, in contradistinction to the severe solubilizations treatments of purified inclusion bodies in the prior art. The solubilizing agent has been found to be compatible with other ingredients encountered in processing of protein aggregates. For example, dithiothreitol, mercaptoethanol, glutathione, cisteine, cistine, dimethylsulfone, urea, thiourea, sodium and potassium hydroxides, borates or mineral acids.

The scope of the invention comprehends the use of all suitable single and multiple chain nitrogen or phosphorous surfactants with various head groups, counter ions and branched or derviatized carbon chains.

Preferably, the at least one cationic, anionic or zwitterionic surfactant is selected, while avoiding combinations of oppositely charged surfactants, from the group consisting Cetyl trimethylammonium halide, e.g. bromide,
Cetyl pyridinium halide, e.g. chloride,
Tetradecyl trimethylammonium halide, e.g. bromide,
Dodecyl trimethylammonium halide, e.g. bromide,
Mixed n-alkyl dimethyl benzyl ammonium halide, e.g. chloride (50% C-14, 40% C-12, 10% C-16),
N,N-dimethyl-N-[2-[2-[4-(1,1,3,3,-tetramethyl butyl) phenoxy]ethoxy]ethyl]benzenemethanaminium halide, e.g. chloride,
Dodecyldimethylamine oxide,
N- lauroylsarcosine sodium salt,
N-lauroyl-N-methyltaurine sodium salt,
N-lauryl-iminodipropionate sodium salt, and
3-(N,N-Dimethyl laurylammonio) propane sulphonate sodium salt.

Where the term halide appears, it should be understood that the selection of the halide ions is illustrative only. The identity of the anion is not critical. For example, other anions may substitue for the halide such as sulfonate and p-toluene sulfonates. In addition, where the term salt appears, the selection of sodium is illustrative only, such that the identity of the cation may not be critical.

More preferably the cationic surfactant is cetyl trimethylammonium bromide or cetyl pyridinium chloride.

It is preferred that the cationic surfactant selected is one which does not absorb in the region of the ultraviolet spectrum where polypeptide absorbance is maximal, for example cetyl trimethylammonium bromide.

The invention provides significant economic advantages in large scale purification systems.

The liquor product so formed includes the desired protein in a soluble form. Where the impurity levels are higher than required, standard purification procedures may be used. Chromatographic procedures are particularly useful.

The method according to the present invention may further comprise the step of separating the solubilized protein from the resulting crude solution.

The separation step may include differential elution of the solubilized protein through a chromatographic column, dialysis, ultrafiltration, differential precipitation, or ligand specific isolation. The chromatographic column may be a high performance liquid chromatography (HPLC) column, optionally a reversed phase high performance liquid chromatography (RP-HPLC) column. A column sold under the trade designation TSK-GEL (LC), (contains a silica gel matrix bonded with a $C_1$ alkyl chain; LC=liquid chromatography) and available from Toyo Soda Manufacturing Co. Ltd. (Japan), or ULTRAPORE RPSC (contains a 5 $\mu$m diameter spherical silica matrix bonded with a $C_3$ alkyl chain; RPSC =reversed phase short chain) available from Beckman Instruments Inc. (California, United States of America), have been found to be suitable. Due to the nature of the solubilizing agent, the separation step may be conducted utilizing other known forms of chromatography, including molecular sieve chromatography gel filtration chromatography, or ion exchange chromatography, hydrophobic interaction chromatography, and ligand specific chromatography. Preferably, the chromatography eluant is an aqueous solution of a cationic, anionic or zwitterionic surfactant. A dilute solution may be used. The cationic, anionic or zwitterionic surfactant may be present in amounts of from approximately 0.25% weight/volume to approximately 2.0% weight/volume, more preferably 0.4% weight/volume.

It will be understood that the chromatographic separation also functions to purify the protein product.

It will also be understood that the method according to the present invention may be utilized in the analysis of a polypeptide sample, wherein the sample to be tested is subjected to the recovery process thereof. The results may provide a quantitative analysis of the composition of the polypeptide sample.

Embodiments of the present invention will now be illustrated with reference to the following non-limiting examples.

EXAMPLE 1

An experiment was conducted with a fermentation liquor, including transformed E.coli cells incorporating inclusion bodies. The E.coli cells contained 1-190AA methionine-porcine growth hormone derived from plasmid pMG939. The cells were concentrated utilizing ultrafiltration techniques, washed twice with an aqueous solution of TRITON X-100 (α[4-(1,1,3,3,-tetramethylbutyl)phenyl]-omega-hydroxypoly(oxy-1,2-ethanediyl)) (0.5%) and EDTA (10 mM), and twice with aqueous EDTA (5 mM).

The cells were treated with aqueous cetyl trimethylammonium bromide (20% w/v), which treatment also effected lysis of the cells. The treatment was conducted in a test tube, and the mixture agitated for 1 hour at room temperature. The mixture was centrifuged (13,000 r.p.m., 10 min) on a Beckman Microfuge II to give a clear supernatant and an insoluble pellet. A small portion of the pellet was fixed and embedded into L.R. White resin and the block section sectioned for comparison by electron microscopy with the untreated material.

The results, in marked contrast to the untreated material, showed that no inclusion bodies were present after the solubilization procedure.

EXAMPLE 2

An experiment was performed with transformed *E. coli* cells containing the expressed variant 4-190AA porcine growth hormone derived from plasmid pMG936. The cells were collected from the fermenter and concentrated by centrifugation (9,000 g, 5 minutes). A portion of the wet cell pellet (50 mg) was vigorously agitated (1h) with N-llauroyl-N-methyltaurine sodium salt (3 ml of 12% w/v) and dithiothreitol (3% w/v) in 0.1M TRIZMA (Tris hydroxymethyl)aminomethane) (pH 10.0), 0.01M EDTA. The mixture was then clarified by centrifugation (50,000 g; 10 minutes). An immuno-dot blot analysis of the clear supernatant using nitro-cellulose paper and a monoclonal antibody to porcine growth hormone confirmed the presence and solubilization into solution of the expressed growth hormone initially contained within the cell.

EXAMPLE 3

An experiment was performed with *E. Coli* cells incorporating inclusion bodies comprising 1-190AA methiomine-porcine growth hormone derived from plasmid pMG939. The cells were isolated from the fermenter broth by centrifugation (9,000 g, 5 minutes). A portion of the wet pellet (50 mg) was then subjected to vigorous agitation (1 h) with an aqueous solution of one of the surfactants listed below (3.0 ml of 10-20% in 0.1M TRIZMA, pH 10.0) in a test tube at 25° C. and in the precence of -mercaptoethanol 2% (v/v). As with previous experiments, substantial solubilization of the inclusion bodies contained initially within the cells had taken place.

(a) cetyl-pyridinium chloride
(b) tetradecyltrimethylammonium bromide
(c) dodecyltrimethylammonium bromide
(d) mixed n-alkyl dimethyl benzyl ammonium chloride (50% C-14, 40% C-12, 10% C-16)
(e) N,N-dimethyl-N-[2-[2-[4-(1,1,3,3-tetramethylbutyl)-phenoxy]ethoxy]ethyl]benzenemethanaminium chloride.
(f) dodecyldimethylamine oxide
(g) N-lauroylsarcosine sodium salt
(h) N-lauroyl-N-methyltaurine sodium salt
(i) N-lauryl-iminodipropionate sodium salt
(j) 3-(N,N-dimethyllaurylammonio)propane sulphonate sodium salt.

Finally, it is to be understood that various other modifications and/or alterations may be made without departing from the spirit of the present invention as outlined herein.

We claim:

1. A method for the recovery of protein in a solubilized form from host cells comprising:
providing a source of host cells incorporating an insoluble synthesized or expressed protein;
providing a source of at least one cationic surfactant; and
treating the host cells with said at least one cationic surfactant in an amount sufficient to effect lysis of the host cell and subsequent solubilization of the insoluble protein to form a solubilized protein, wherein said cationic surfactant includes a cation selected from the group consisting of cetyl trimethylammonium cations, cetyl pyridinium cations, tetradecyl trimethylammonium cations, dodecyl trimethylammonium cations, mixed n-alkyl dimethyl benzyl ammonium cations and N,N-dimethyl-N-[2-[2-[4-(1,1,3,3,-tetramethylbutyl)phenoxy]ethoxy]ethyl]benzenemethanaminium cations.

2. A method according to claim 1 wherein said insoluble synthesized or expressed protein is selected from the group consisting of growth hormones, interferons, immunogens, and lymphokines.

3. A method according to claim 2 wherein said at least one cationic surfactant is present in an amount of approximately 2.5-50% weight for volume.

4. A method according to claim 3 wherein said cationic surfactant is cetyl trimethylammonium bromide.

5. A method according to claim 4 wherein said at least one cationic surfactant is present in an amount exceeding the micelle concentration.

6. A method according to claim 3 further comprising the step of separating the solubilized protein, wherein the separation step is selected from the group consisting of differential elution of the solubilized protein through a chromatographic column, dialysis, ultrafiltration, and differential precipitation.

* * * * *

UNITED STATES PATENT AND TRADEMARK OFFICE
CERTIFICATE OF CORRECTION

PATENT NO. : 4,992,531
DATED : February 12, 1991
INVENTOR(S) : J.J. Patroni et al.

It is certified that error appears in the above-identified patent and that said Letters Patent is hereby corrected as shown below:

Column 2, line 34, for "orvine" read --ovine--;

Column 2, line 50, after "optimal" insert --recovery--;

Column 2, line 54, for "solubiling" read --solubilizing--;

Column 2, line 68, after "the" (first occurrence) read --solubilized--.

Column 3, line 10, for "More, preferably" read --More preferably,--;

Column 3, line 53, after "consisting" insert --of--;

Column 4, line 4, for "substitue" read --substitute--;

Column 4, line 44, after "chromatography" insert --, such as--;

Column 5, line 33, after "Tris" insert --(--.

Signed and Sealed this

Sixth Day of October, 1992

Attest:

DOUGLAS B. COMER

*Attesting Officer*       Acting Commissioner of Patents and Trademarks